United States Patent [19]

Wu

[11] Patent Number: 5,365,007

[45] Date of Patent: Nov. 15, 1994

[54] ETHYLENE OLIGOMERIZATION AND CATALYST THEREFOR

[75] Inventor: An-hsiang Wu, Bartlesville, Okla.

[73] Assignee: Phillips Petroleum Company, Bartlesville, Okla.

[21] Appl. No.: 113,039

[22] Filed: Aug. 31, 1993

Related U.S. Application Data

[62] Division of Ser. No. 985,713.

[51] Int. Cl.$^5$ .......................... C07C 2/08; C07C 2/18
[52] U.S. Cl. .................................. 585/528; 585/514; 585/527
[58] Field of Search ............... 585/510, 511, 514, 520, 585/527, 528

[56] References Cited

U.S. PATENT DOCUMENTS

| | | | |
|---|---|---|---|
| 3,644,564 | 2/1972 | Zwet et al. | 260/683.15 D |
| 3,647,915 | 3/1972 | Bauer et al. | 260/683.15 D |
| 4,482,640 | 11/1984 | Knudsen et al. | 502/155 |
| 5,104,841 | 4/1992 | Conroy et al. | 502/158 |

Primary Examiner—Asok Pal
Assistant Examiner—P. Achutamurthy
Attorney, Agent, or Firm—Lucas K. Shay

[57] ABSTRACT

A composition and a process for catalyzing ethylene oligomerization employing the composition as catalyst are disclosed. The composition comprises a nickel compound, a phosphine compound, and a phosphated alumina where the phosphated alumina is both a component of and a support for the composition. The ethylene oligomerization process comprises (1) combining a nickel compound and a phosphine compound in a solvent to form a mixture; (2) combining the mixture with a phosphated alumina under ethylene pressure to form a catalyst system; (3) contacting ethylene with the catalyst system under oligomerization conditions to produce higher olefins having more than 2 carbon atoms.

32 Claims, No Drawings

ETHYLENE OLIGOMERIZATION AND CATALYST THEREFOR

This application is a division of application Ser. No. 07/985,713, filed Dec. 4, 1992, now U.S. Pat. No. 5,228,986.

FIELD OF THE INVENTION

The present invention relates to ethylene oligomerization process to produce higher olefins and a heterogeneous catalyst useful for the oligomerization process.

BACKGROUND OF THE INVENTION

Many catalysts containing a nickel compound are known to oligomerize ethylene to higher olefins. For example, U.S. Pat. No. 4,482,640 discloses a process for the oligomerization of ethylene using a homogeneous catalyst consisting essentially of a nickel compound, a phosphine compound, and an acid; U.S. Pat. No. 3,647,915 discloses an ethylene oligomerization catalyst comprising an atom of nickel chelated with a chelating ligand having a tertiary organophosphine moiety and a carbonyl ligand; and U.S. Pat. No. 3,644,564 discloses ethylene oligomerization in the presence of a catalyst comprising nickel(0) complexed with a fluorine-containing ligand.

While the catalyst systems discussed above are operable for ethylene oligomerization, they are either homogeneous catalyst systems that are not suitable for continuous processes or relatively expensive. Additionally, some of the known ethylene oligomerization processes require long reaction time, high temperature, or both, to achieve satisfactory results. Furthermore, by using a known ethylene oligomerization process, one has not always achieved high catalyst productivity and good product selectivity. Finally, because of the increasing importance of higher olefins in chemical industries, for example, 1-butene as industrial feedstock, 1-hexene as comonomer for polyethylenes production, and 1-decene as comonomer for high temperature polyolefins, processes and catalysts that make even slight improvements in the availability of these olefins over the known processes and catalysts are highly desirable.

SUMMARY OF THE INVENTION

Therefore, an object of the present invention is to provide a composition for catalyzing ethylene oligomerization. Another object of the invention is to provide a process for preparing the composition. A further object of the invention is to provide a process for ethylene oligomerization. An advantage of the invention is the production of 1-olefins with high selectivity at mild temperatures. Another advantage of the present invention is the use of a heterogeneous composition that can be easily employed in a continuous process for ethylene oligomerization. Other objects, advantages, and features of the invention will become more apparent as the invention is more fully disclosed hereinbelow.

According to a first embodiment of the present invention, a composition useful for ethylene oligomerization is provided which comprises a nickel compound, a phosphine compound, and a phosphated alumina.

According to a second embodiment of the invention, a process for ethylene oligomerization is provided which comprises: (1) combining a nickel compound and a phosphine compound in a solvent to form a mixture; (2) combining the mixture with a phosphated alumina under ethylene pressure to form a catalyst system; (3) contacting ethylene with the catalyst system under oligomerization conditions to produce higher olefins having more than 2 carbon atoms; and (4) recovering the higher olefins.

DETAILED DESCRIPTION OF THE INVENTION

The present invention provides a composition comprising a nickel compound, a phosphine compound, and an aluminum phosphate. The preferred nickel compound has s nickel atom complexed with at least one organic moiety and the nickel atom has a valent state of 0. Examples of the presently preferred nickel compound include, but are not limited to, bis(1,5-cyclooctadiene)-nickel(0), bis(tricyclohexylphosphine)nickel(0), nickel(0) tetracarbonyl, (cyclododecatriene)nickel(0), bis(ethylene)(di-cyclohexylphosphine)nickel(0), tris(tricyclohexylphosphine)nickel(0), tetrakis(trifluorophosphine)nickel(0), tetrakis(triphenylphosphine) nickel(0), and mixtures thereof. The presently most preferred nickel compound is bis(1,5-cyclooctadiene)nickel(0).

The phosphine compound suitable for the present invention has the formula of $PR_3$, where R independently represents H or a $C_1$ to $C_{20}$ hydrocarbyl radical and where at least one R is not H. Examples of suitable phosphine compounds include, but are not limited to, cyclohexylphosphine, dicyclohexylphosphine, tricyclohexylphosphine, triethylphosphine, triisopropylphosphine, triisobutylphosphine, tri-n-butylphosphine, tri-t-butylphosphine, diphenylphosphine, triphenylphosphine, diphenylcyclohexylphosphine, diethylphenylphosphine, ortho-tolyldiphenylphosphine, di(ortho-tolyl)phenylphosphine, tribenzylphosphine, and mixtures thereof. Dicyclohexylphosphine is presently preferred.

The phosphated alumina useful for the present invention can be prepared by the steps comprising: (1) mixing aluminum nitrate with a phosphate compound, in the present of water, to form a solution; (2) adding a basic compound, preferably in aqueous form, to the solution to produce a solid product; (3) recovering the solid product; (4) optionally, washing the solid product with a solvent to prepare a washed-product; (5) drying the solid product or washed product, resulting in a dried product; and (6) calcining the dried product to produce the phosphated alumina. Suitable phosphate compounds include, but are not limited to ammonium phosphate (dibasic), ammonium phosphate (monobasic), sodium phosphate (monobasic), sodium phosphate (dibasic), magnesium phosphate, potassium phosphate (dibasic), potassium phosphate (monobasic), manganese phosphate, and mixtures thereof. The presently preferred phosphate compound is ammonium phosphate (monobasic) because of its ready availability and ease of use. Suitable basic compound employed in step (2) should be able to produce a precipitate from the solution. Examples of suitable basic compound include, but are not limited to, ammonium hydroxide, lithium hydroxide, sodium hydroxide, sodium carbonate, sodium bicarbonate, potassium hydroxide, magnesium hydroxide, barium phenoxide, calcium hydroxide, calcium phenoxide, RONa, RSNa, and mixtures thereof wherein R is a $C_1$–$C_6$ alkyl radial. The presently preferred basic compound is ammonium hydroxide. The solvent used in step (4) to wash the solid product can be an alcohol, either, ketone, acid, amide, or water, as long as it does not react with or solubilize the solid product. Examples of suitable solvent include, but are not limited to water, methanol, ethanol, propanol, isopropanol, butanol, isobutanol, pentanol, diethyl ether, tetrahydrofuran, acetone, methyl ethyl ketone, acetic acid, dimethylforamide, and mixtures thereof. The presently preferred solvents are water and ethanol because of their ready availability. The drying of step (5) can be a conventional drying or drying under reduced pressure. The drying temperature can vary widely from about 50° C. to about 150° C. under about 0.05 mmHg to about 800 mmHg pressure for about 1 to about 30 hours, preferably from 60° C. to 100° C. under 0.05 to 760 mmHg pressure for 5 to 20 hours. The calcining step can also vary widely from about 250° C. to about 1500° C., preferably 500° C. to 1000° C., under atmospheric pressure for about 30 minutes to about 15 hours, preferably 1 to 7 hours.

In the preparation of the phosphated alumina, the molar ratio of the phosphate compound to aluminum nitrate is generally in the range of from about 0.05:1 to about 5:1, preferably from about 0.1:1 to about 2:1, and most preferably from 0.2:1 to 1:1 for best physical form and catalytic activity of phosphated alumina when used as a component of the invention composition. The molar ratio of water to aluminum nitrate is in the range of from about 10:1 to about 200:1, depending on the solubility of both aluminum and the phosphate compound, preferably about 20:1 to about 100:1, most preferably 25:1 to 50:1. The molar ratio of the basic compound to aluminum nitrate is in the range of from about 0.05:1 to about 10:1, preferably about 0.2:1 to about 5:1 and most preferably 0.5:1 to 2:1. The recovery of the solid product in step (3) can be carried out by any known means such as, for example, filtration, decantation and centrifugation. The molar ratio of the washing solvent to aluminum nitrate can vary widely from about 5:1 to about 1000:1 depending on the type of solvent used. The washing can also be carried out more than once and/or with a different solvent.

In the preparation of the composition of the invention, the molar ratio of the phosphine compound to the nickel compound suitable for the invention is generally about 0.1:1 to about 2:1, preferably about 0.5:1 to about 1.5:1, and most preferably 0.8:1 to 1.2:1. The suitable weight ratio of the phosphated alumina to the nickel compound is about 1:1 to about 200:]preferably about 5:1 to about 100:1, and most preferably 10:1 to 60:1. The weight ratio of the solvent to the nickel compound is in the range of about 1:1 to about 2000:1, preferably about 5:1 to about 800:1 and most preferably 10:1 to 600:1.

The composition of the invention can be generally prepared by first forming a mixture of the nickel compound and phosphine compound in a solvent at about 0° C. to about 100° C., preferably at about 5° C. to about 75° C., and most preferably from 10° C. to 50° C., under ethylene atmosphere, for about 5 minutes to about 5 hours, preferably about 10 minutes to about 4 hours, and most preferably from 20 minutes to 2 hours. The ethylene pressure is about 10 psig to about 1000 psig, preferably about 15 psig to about 1000 psig, and most preferably 20 psig to 800 psig. A variety of solvents such as, for example, hydrocarbon, alcohol, ketone, amide, ether, and mixtures thereof, can be used as solvent for the present invention. The preferred solvent is a hydrocarbon which includes, but is not limited to, benzene, toluene, p-xylene, o-xylene, m-xylene, ethylbenzene, propylbenzene, p-ethyltoluene, styrene, phenylacetylene, fluorobenzene, trifluorotoluene, butane, pentane, hexane, heptane, octane, decane, cyclohexane, and mixtures thereof.

A phosphated alumina, prepared by the process described above, is then combined with the mixture of the nickel compound and phosphine compound, under ethylene pressure in the range of from about 10 psig to about 1000 psig, preferably about 15 psig to about 1000 psig, and most preferably 20 psig to 800 psig and at a temperature in the range of from about 0° C. to about 200° C., preferably 5° C. to about 100° C. and most preferably 10° C. to 75° C. The ethylene oligomerization reaction generally takes place once ethylene is contacted with the composition of the invention, i.e., the combining of the phosphated alumina and the solution of the nickel compound and phosphine compound. Ethylene oligomerization can be carried out in a batch mode or in a continuous mode by continuously contacting ethylene with the composition of the invention. The time required for ethylene oligomerization is in the range of from about 5 minutes to about 10 hours, preferably about 10 minutes to 5 hours, and most preferably from 20 minutes to 3 hours to ensure complete reaction and high selectivity to 1-olefins. The ethylene oligomerization products generally contain olefins having more than 2 carbon atoms, up to about 24 carbon atoms.

Finally, the oligomerization products as contained in the reaction mixture can be separated and recovered from the catalyst by conventional means such as fractionation distillation.

Any appropriate vessels that can be pressurized and maintain high pressure to 5000 psig can be used in the dimerization process of the invention. Preferred vessels are stainless steel reactors equipped with inlet valves for pressurizing the vessel with ethylene, which also serves as the reactant, for addition of the catalyst components, and for discharging the catalyst components as well as reaction mixtures; agitation means such as power agitator for mixing; temperature control means such as a jacket or inner heat exchangers; and other optionally equipment. The type of vessels suitable for carrying out the invention is a matter of choice for one skilled in the art.

EXAMPLES

Examples are set forth below to further illustrate the invention but are not be be construed to limit the invention in any manner.

Each example employed at least one 300 ml stainless steel (316SS) Autoclave Engineers stirred tank autoclave, hereafter referred to simply as a reactor. Other equipment employed in individual examples will be referenced in those examples. It is understood that the contents of such reactor(s) in the following examples are being agitated, typically at a slow agitation of about 300 rpm during purging of the reactor or addition of various reagents to the reactor, and at a normal agitation of about 1700 rpm at all other times.

Product analysis was performed on approximately 5 gram samples (collected in a stainless sample tube) with an HP 5890 II GC-FID Spectrometer equipped with a capillary DB-1 (60 m) column. The column was operated at 30° C. for 5 minutes, followed by a 15° C./minute increase to 285° C. which as held for 13 minutes. Samples were injected into the GC through an on-line filter. Detection was obtained using a flame ionization detector in the area percent mode. Selectivity and weight percent distribution, discussed further below, were determined from spectra as recorded by the spectrometer.

EXAMPLE I

This example illustrates the preparation of a phosphated alumina.

Aluminum nitrate nonahydrate ($Al(NO_3)_3 \cdot 9H_2O$; 37.5 g; 0.1 mole) and ammonium phosphate monobasic (($NH_4)H_2PO_4$; 4.6 g; 0.04 mole) were mixed and dissolved in 50 ml $H_2O$ in a 400 ml beaker. Upon forming a homogeneous solution, ammonium hydroxide (28%; 10 ml) was added to the solution while the solution was being agitated with a glass rod. Shortly thereafter, a white precipitate was formed. The precipitate was recovered by filtration, washed with ethanol (3 times, 50 ml each) and then with water (3 times, 50 ml each), dried in a vacuum oven (80° C., 0.1 mmHg), and then calcined at 700° C. for 3 hours in a furnace. Total weight of calcined product was 7.42 g. Fleshly prepared phosphated alumina was used for the preparation of the inventive composition which as then used for ethylene oligomerization reaction.

EXAMPLE II

This example illustrates the oligomerization process of the invention using the inventive composition as catalyst with dicyclohexylphosphine as the phosphine component. The amount of each chemical and reaction conditions are shown in Table I.

In a 300 ml stainless steel reactor equipped with an addition valve which was connected with an addition sample vessel. The reactor was purged with nitrogen 5 times (about 1 minute each time) followed by addition of bis(1,5-cyclooctadiene)nickel(0), dicyclohexylphosphine and 50 ml of freshly distilled hydrocarbon solvent (shown in table I) in an argon-filled dry box. The reactor was then sealed, purged with ethylene at least 5 times (about 1 minute each time) and pressurized with ethylene to 600–700 psig (see Table I below) followed by agitation (1700 rpm) for 60 minutes at 50° C. This reactor was labeled reactor 1.

A separated sealed reactor, equipped the same as reactor 1 and having been purged with argon 5 times (about 1 minute each time), was labeled reactor 2 and was used for ethylene oligomerization. Freshly calcined phosphated alumina as prepared in Example I was added to reactor 2. The homogeneous solution of reactor 1 was then added to rector 2 under ethylene pressure through the addition valve, while agitated (1700 rpm) along with ethylene (600–700 psig, see Table I). All runs were carried out at 50° C. In Table I, results are reported in terms of productivity, selectivity to 1-decene and weight percent distribution of olefins. Productivity is defined as grams of oligomerization product produced per gram of the nickel compound per hour, and was calculated in each example based on grams of ethylene reacted. Selectivity to 1-decene is given in terms of the weight percent of 1-decene of total decenes produced and is used as an indication of catalyst selectivity to 1-olefins. The distribution of the olefins is given as the weight percent of each olefin of total oligomerized product.

TABLE I

| | | | | Ethylene Oligomerization | | | | | | | | |
|---|---|---|---|---|---|---|---|---|---|---|---|---|
| Run # | Wt (g) $Ni(COD)_2{}^a$ | Wt (g) $PO_4$—$Al_2O_3{}^c$ | Wt (g) HP $(C_6H_{11})_2{}^b$ | Solvent | Ethylene Press (psig) | Rxn Time (h) | Productivity g/g/h | $C_4$ | $C_6$ | Wt % Olefin $C_8$ | $C_{10}$ | $C_{12}+{}^d$ | 1-olefin Selectivity$^e$ |
| 1 | 0.15 | 4.78 | 0.11 | benzene | 700 | 2 | 462 | 66 | 18 | 8 | 4 | 4 | 83 |
| 2 | 0.15 | 5.11 | 0.11 | fluorobenzene | 600 | 2 | 471 | 62 | 19 | 9 | 4 | 6 | 80 |
| 3 | 0.15 | 4.50 | 0.10 | toluene | 600 | 1 | 509 | 69 | 17 | 6 | 4 | 4 | 83 |
| 4 | 0.15 | 5.00 | 0.11 | p-Xylene | 650 | 1 | 540 | 63 | 20 | 8 | 4 | 5 | 85 |
| 5 | 0.15 | 5.20 | 0.11 | trifluorobenzene | 700 | 1 | 680 | 62 | 22 | 10 | 4 | 2 | 84 |
| 6 | 0.15 | 4.75 | 0.11 | n-pentane | 700 | 1 | 580 | 66 | 15 | 8 | 5 | 6 | 86 |
| 7 | 0.15 | 5.15 | 0.11 | n-heptane | 700 | 1 | 720 | 60 | 24 | 10 | 3 | 3 | 81 |
| 8 | 0.10 | 4.00 | 0.00 | toluene | 700 | 2 | 0 | 0 | 0 | 0 | 0 | 0 | — |
| 9 | 0.10 | 0.00 | 0.07 | toluene | 700 | 2 | 0 | 0 | 0 | 0 | 0 | 0 | — |

$^a Ni(COD)_2$, bis(1,5-cyclooctadiene)nickel(0).
$^b HP(C_6H_{11})_2$, dicyclohexylphosphine.
$^c AlPO_4$, phosphated alumina as prepared in Example I.
$^d C_{12}+$ represents wt % of $C_{12}$ and higher olefins.
$^e$Selectivity was calculated as described in the text.

The results show that the catalyst productivity ranged from 462 g/g/hr, when benzene was used as solvent (run 1) to as high as 720 g/g/hr, when heptane was used as solvent (run 7). The majority of the oligomerization products were butenes (60% or higher) and had high selectivity (80% or higher) to 1-olefins as measured by 1-decene. Two control runs (runs 8–9) were included in the runs to show that without either a phosphine compound (run 8) or a phosphated alumina (run 9), no ethylene oligomerization reaction was detected. Table I also shows that, even at higher ethylene pressure and longer reaction time, no oligomerization occurred in control runs 8–9 (compared with run 3 which had same reaction conditions as runs 8–9 except that the reaction time was only 1 hour).

The results shown in the above examples clearly demonstrate that the present invention is well adapted to carry out the objects and attain the ends and advantages mentioned as well as those inherent therein. While modifications may be made by those skilled in the art, such modifications are encompassed within the spirit of the present invention as defined by the specification and the claims.

That which is claimed is:

1. A process for ethylene oligomerization comprising: (1) combining a nickel compound and a phosphine compound in a solvent to form a mixture; (2) combining said mixture with a phosphated alumina to form a catalyst system; and (3) contacting ethylene with said catalyst system under oligomerization conditions to produce an olefin having more than 2 carbon atoms.

2. A process according to claim 1 further comprising recovering said olefin.

3. A process according to claim 1 wherein said olefin is selected from the group consisting of butenes, hexenes, octenes, decenes, olefins having more than 10 carbon atoms, and mixtures thereof.

4. A process according to claim 1 wherein said nickel compound is selected from the group consisting of bis(1,5-cyclooctadiene)nickel(0), bis(tricyclohexylphosphine)nickel(0), nickel(0) tetracarbonyl, (cyclododecatriene)nickel(0), bis(ethylene)(dicyclohexylphosphine)nickel(0), tris(tricyclohexylphosphine)nickel(0), tetrakis(trifluorophosphine)nickel(0), tetrakis(triphenylphosphine) nickel(0), and combinations of two or more thereof.

5. A process according to claim 4 wherein said nickel compound is bis(1,S-cyclooctadiene)nickel(0).

6. A process according to claim 1 wherein said phosphine compound has the formula of $PR_3$ wherein each R is selected from the group consisting of hydrogen, a $C_1$ to $C_{20}$ hydrocarbyl radical, and combinations of two ore more thereof and at least one R is not hydrogen.

7. A process according to claim 1 wherein said phosphine compound is selected from the group consisting of cyclohexylphosphine, dicyclohexylphosphine, tricyclohexylphosphine, triethylphosphine, triisopropylphosphine, triisobutylphosphine, tri-n-butylphosphine, tri-t-butylphosphine, diphenylphosphine, triphenylphosphine, diphenylcyclohexylphosphine, diethylphenylphosphine, ortho-tolyldiphenylphosphine, di(ortho-tolyl)phenylphosphine, tribenzylphosphine, and mixtures thereof.

8. A process according to claim 7 wherein said phosphine compound is dicyclohexylphosphine.

9. A process according to claim 1 wherein said phosphated alumina is prepared by the steps comprising: (1) mixing aluminum nitrate with a phosphate compound, in the present of water, to form a solution; (2) adding a basic compound, preferably in aqueous form, to said solution to produce a solid product; (3) recovering said solid product; (4) drying said solid product, resulting in a dried product; and (5) calcining said dried product to produce the phosphated alumina.

10. A process according to claim 9 wherein said phosphate compound is ammonium phosphate, monobasic.

11. A process according to claim 9 wherein said basic compound is ammonium hydroxide.

12. A process according to claim 9 wherein the molar ratio of said phosphate compound to aluminum nitrate is from 0.2:1 to 1: 1.

13. A process according to claim 1 wherein the molar ratio of said phosphine compound to said nickel compound is in the range of from about 0.1: 1 to about 2: 1.

14. A process according to claim 13 wherein said molar ratio is in the range of from about 0.5:1 to about 1.5:1.

15. A process according to claim 14 wherein said molar ratio is in the range of from 0.8:1 to 1.2:1.

16. A process according to claim 1 wherein the weight ratio of said phosphated alumina to said nickel compound is in the range of from about 1: 1 to about 200: 1.

17. A process according to claim 16 wherein said weight ratio is in the range of from about 5:1 to about 100: 1.

18. A process according to claim 17 wherein said weight ratio is in the range of from 10:1 to 60:1.

19. A process according to claim 1 wherein the molar ratio of said phosphine compound to said nickel compound is in the range of from 0.8:1 to 1.2:1 and the weight ratio of said phosphated alumina to said nickel compound is in the range of from 10:1 to 60: 1.

20. A process according to claim 1 wherein said solvent is selected from the group consisting of benzene, toluene, p-xylene, o-xylene, m-xylene, ethylbenzene, propylbenzene, p-ethyltoluene, styrene, phenylacetylene, fluorobenzene, trifluorotoluene, butane, pentane, hexane, heptane, octane, decane, cyclohexane, and mixtures thereof.

21. A process according to claim 1 wherein said solvent is selected from the group consisting of benzene, fluorobenzene, toluene, p-xylene, trifluorobenzene, n-pentane, n-heptane, and combinations thereof.

22. A process according claim 1 wherein said combining of the nickel compound and the phosphine compound is carried out at a temperature in the range of from about 0° C. to about 100° C.

23. A process according to claim 22 wherein said range is from about 5° C. to about 75° C.

24. A process according to claim 23 wherein said range is from 10° C. to 50° C.

25. A process according to claim 1 wherein said combining of said mixture is with phosphated alumina is carried out at a temperature in the range of from about 0° C. to about 200° C.

26. A process according to claim 25 wherein said range is from about 5° C. to about 100° C.

27. A process according to claim 26 wherein said range is from 10° C. to 75° C.

28. A process according to claim 1 wherein said process is carried out under a pressure in the range of from about 10 psig to about 100 psig.

29. A process according to claim 28 wherein said range is from 20 psig to 800 psig.

30. A process according to claim 1 wherein said process comprises: (1) combining a nickel compound with a phosphine compound in a hydrocarbon solvent, at 10° C. to 50° C. under an ethylene pressure in the range of 20 psig to 800 psig for 20 minutes to 2 hours to form a mixture; wherein the molar ratio of said phosphine compound to said nickel compound in in the range of from 0.8:1 to 1.2:1 and the ratio of said solvent to said nickel compound is in the range of from 10:1 to 600:1; (2) combining said mixture with a phosphated alumina, at 10° C. to 75° C. under an ethylene pressure in the range of from 20 psig to 800 psig for 2 minutes to 3 hours, to produce olefins having greater than 2 carbon atoms; wherein the weight ratio of said phosphated alumina to said nickel compound is in the range of from 10:1 to 60:1; and (3) recovering said olefins.

31. A process according to claim 30 wherein said nickel compound is bis(1,5-cyclooctadiene)nickel(0), said phosphine compound is dicyclohexylphosphine and said solvent is selected from the group consisting of benzene, fluorobenzene, toluene, p-xylene, trifluorobenzene, n-pentane, n-heptane, and combinations thereof.

32. A process comprising: (1) combining bis(1,5-cyclooctadiene)nickel(0) with a dicyclohexylphosphine in a hydrocarbon solvent, at 10° C. to 50° C. under an ethylene pressure in the range of 20 psig to 800 psig for 20 minutes to 2 hours to form a mixture; wherein the molar ratio of said dicyclohexylphosphine to said bis(1,5-cyclooctadiene)nickel(0) is in the range of from 0.8:1 to 1.2:1 and the weight ratio of said solvent to said bis(1,5-cyclooctadiene)nickel(0) is in the range of from 10:1 to 600:1; (2) combining said mixture with a phosphated alumina, at 10° C. to 75° C. under an ethylene pressure in the range of from 20 psig to 800 psig for 2 minutes to 3 hours, to produce olefins having greater than 2 carbon atoms; wherein the weight ratio of said phosphated alumina to said bis(1,5-cyclooctadiene)nickel(0) is in the range of from 10:1 to 60:1; and (3) recovering said olefins.

* * * * *

UNITED STATES PATENT AND TRADEMARK OFFICE
CERTIFICATE OF CORRECTION

PATENT NO. : 5,365,007
DATED : November 15, 1994
INVENTOR(S) : An-hsiang Wu

It is certified that error appears in the above-indentified patent and that said Letters Patent is hereby corrected as shown below:

Column 7, line 13, please delete "bis(1-5-cyclooctadiene)nickel(0)" and insert therefor --bis(1,5-cyclooctadiene)nickel(0)--.

Signed and Sealed this

Seventh Day of February, 1995

Attest:

BRUCE LEHMAN

Attesting Officer

Commissioner of Patents and Trademarks